United States Patent [19]

Chang

[11] Patent Number: 4,959,095
[45] Date of Patent: Sep. 25, 1990

[54] HERBICIDAL O-CARBOMETHOXYSULFONYLUREA

[75] Inventor: Siew H. Chang, Kuala Lumpur, Malaysia

[73] Assignee: E. I. Du Pont de Nemours and Company, Wilmington, Del.

[21] Appl. No.: 258,555

[22] Filed: Oct. 19, 1988

Related U.S. Application Data

[63] Continuation of Ser. No. 125,302, Nov. 25, 1987, abandoned.

[51] Int. Cl.$^5$ .............................................. A01N 43/64
[52] U.S. Cl. ........................................... 71/93; 71/86
[58] Field of Search ............................................ 71/93

[56] References Cited

U.S. PATENT DOCUMENTS 4,383,113  5/1983  Levitt .................... 544/211

*Primary Examiner*—Glennon H. Hollrah
*Assistant Examiner*—Eric J. Kraus
*Attorney, Agent, or Firm*—James A. Costello

[57] ABSTRACT

The compound methyl 2-[[[[(4-methoxy-6-methyl-1,3,5-triazin-2-yl)amino]carbonyl]amino]sulfonyl]benzoate has high herbicidal activity and is particularly useful for weed control in plantation crops.

4 Claims, No Drawings

HERBICIDAL O-CARBOMETHOXYSULFONYLUREA

This application is a continuation of U.S. application Ser. No. 125,302, filed Nov. 25, 1987, which is now abandoned.

BACKGROUND OF THE INVENTION

The compound methyl 2-[[[[(4-methoxy-6-methyl-1,3,5-triazin-2-yl)amino]carbonyl]amino]sulfonyl]-benzoate has high herbicidal activity and a desirable spectrum of weed control for use in plantation crops.

The compound of interest is disclosed in U.S. Pat. No. 4,383,113, for uses other than weed control in plantation crops.

SUMMARY OF THE INVENTION

This invention pertains to the use of the compound of Formula I and its agriculturally suitable salts for broad spectrum weed control in plantation crops.

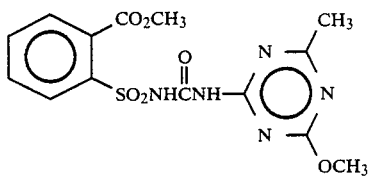

The compound is methyl 2-[[[[(4-methoxy-6-methyl-1,3,5-triazin-2-yl)amino]carbonyl]amino]-sulfonyl]benzoate.

SYNTHESIS

The title compound of Formula I (metsulfuron methyl) can be prepared according to the procedure disclosed in U.S. Pat. No. 4,383,113 as follows:

EXAMPLE 1

To an anhydrous suspension of 1.4 g of 2-amino-4-methoxy-6-methyl-1,3,5-triazine in 25 ml of methylene chloride is added with stirring at ambient temperature and pressure 2.4 g of 2-methoxycarbonylbenzenesulfonylisocyanate. The mixture is thereafter stirred for 16 hours and filtered. The filtrate is evaporated to dryness, the residue is triturated with butyl chloride and the product removed by filtration.

FORMULATIONS

Useful formulations of the compound of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents," Chemical Publishing Co., Inc., New York, 1964, list surfactants and recommended uses. All formulations can contain minor amounts of additives to reduce foaming, caking, corrosion, microbiological growth, and the like.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See Browning, "Agglomeration", *Chemical Engineering*, Dec. 4, 1967, pp. 147ff. and "Perry's Chemical Engineer's Handbook", 5th Ed., McGraw-Hill, New York, 1973, pages 8 to 57 and following.

For further information regarding the art of formulation, see for example: U.S. Pat. No. 3,235,361, column 6, line 16 through column 7, line 19 and Examples 10 through 41; U.S. Pat. No. 3,309,192, column 5, line 43 through column 7, line 62 and Examples 8, 12, 15, 39, 41, 52, 53, 58, 132, 138 to 140, 162 to 164, 166, 167 and 169 to 182; U.S. Pat. No. 2,891,855, column 3, line 66 through column 5, line 17 and Examples 1 to 4; Klingman, "Weed Control as a Science", John Wiley and Sons, Inc., New York, 1961, pages 81 to 96; and Fryer et al., "Weed Control Handbook", 5th Ed., Blackwell Scientific Publications, Oxford, 1968, pages 101 to 103.

In the following Examples, all parts are by weight unless otherwise indicated.

EXAMPLE 2

| Wettable Powder | |
|---|---|
| Methyl 2-[[[[(4-methoxy-6-methyl-1,3,5-triazin-2-yl)-amino]carbonyl]amino]sulfonyl]benzoate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 3

| Granule | |
|---|---|
| Wettable Powder of Example 2 | 5% |
| attapulgite granules (U.S.S. 20 to 40 mesh; 0.84 to 0.42 mm) | 95% |

A slurry of wettable powder containing 25% solids is sprayed on the surface of attapulgite granules in a double-cone blender. The granules are dried and packaged.

EXAMPLE 4

| Extruded Pellet | |
|---|---|
| Methyl 2-[[[[(4-methoxy-6-methyl-1,3,5-triazin-2-yl)-amino]carbonyl]amino]sulfonyl]benzoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 5

| Low Strength Granule | |
|---|---|
| Methyl 2-[[[[(4-methoxy-6-methyl-1,3,5-triazin-2-yl)-amino]carbonyl]amino]sulfonyl]benzoate | 1% |
| N,N-dimethylformamide | 9% |
| attapulgite granule (U.S.S. 20 to 40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 6

| Aqueous Suspension | |
|---|---|
| Methyl 2-[[[[(4-methoxy-6-methyl-1,3,5-triazin-2-yl)-amino]carbonyl]amino]sulfonyl]benzoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 7

| Oil Suspension | |
|---|---|
| Methyl 2-[[[[(4-methoxy-6-methyl-1,3,5-triazin-2-yl)-amino]carbonyl]amino]sulfonyl]benzoate | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 8

| Granule | |
|---|---|
| Methyl 2-[[[[(4-methoxy-6-methyl-1,3,5-triazin-2-yl)-amino]carbonyl]amino]sulfonyl]benzoate | 80% |
| wetting agent | 1% |
| crude ligninsulfonate salt (containing 5 to 20% of the natural sugars) | 10% |
| attapulgite clay | 9 |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14 to 100 mesh (1410 to 149 microns), and packaged for use.

EXAMPLE 9

| High Strength Concentrate | |
|---|---|
| Methyl 2-[[[[(4-methoxy-6-methyl-1,3,5-triazin-2-yl)-amino]carbonyl]amino]sulfonyl]benzoate | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 10

| Wettable Powder | |
|---|---|
| Methyl 2-[[[[(4-methoxy-6-methyl-1,3,5-triazin-2-yl)- | 90% |

| -continued |  |
|---|---|
| Wettable Powder |  |
| amino]carbonyl]amino]sulfonyl]benzoate |  |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 11

| Wettable Powder |  |
|---|---|
| Methyl 2-[[[[(4-methoxy-6-methyl-1,3,5-triazin-2-yl)-amino]carbonyl]amino]sulfonyl]benzoate | 20% |
| sodium ligninsulfonate | 20% |
| montmorillonite clay | 60% |

The ingredients are thoroughly blended, coarsely hammer-milled and then air-milled to produce particles essentially all below 10 microns in size. The material is reblended and then packaged.

EXAMPLE 12

| Dust |  |
|---|---|
| Methyl 2-[[[[(4-methoxy-6-methyl-1,3,5-triazin-2-yl)-amino]carbonyl]amino]sulfonyl]benzoate | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

The compound of this invention can be specially formulated with diluents and/or carriers and/or other pesticides for application to plantation crops. The following list exemplifies some of the herbicides suitable for use in mixtures.

| Common Name | Chemical Name |
|---|---|
| dalapon | 2,2-dichloropropionic acid |
| diuron | 3-(3,4-dichlorophenyl)-1,1-dimethylurea |
| DSMA | disodium methanearsonate |
| glufosinate | 4-[hydroxy(methyl)phosphinoyl]-DL-homo-alanine and its agriculturally suitable salts especially the ammonium salt |
| glyphosate | N-(phosphonomethyl)glycine and herbicidally, acceptable salts especially the mono(isopropylammonium) and tri-methylsulfonium salts |
| hexazinone | 3-cyclohexyl-6-(dimethylamino)-1-methyl-1,3,5-triazine-2,4(1H,3H)dione |
| MSMA | monosodium methanearsonate |
| paraquat | 1,1'-dimethyl-4,4'-bipyridinium ion |
| triclopyr | 3,5,6-trichloro-2-pyridyloxyacetic acid |
| 2,4-D | (2,4-diclorophenoxy)acetic acid and its agriculturally suitable salts especially the dimethyl ammonium salt |
| 2,4-DB | 4-(2,4-dichlorophenoxy)butyric acid |
| imazapyr-isopropyl-ammonium | 2-(4-isopropyl-4-methyl-5-oxo-2-imida-zolin-2-yl)nicotinic acid with iso-propyl amine (1:1) |
| picloram | 4-amino-3,5,6-trichloropicolinic acid |

UTILITY

The compound employed in the method of the present invention is an active herbicide for selective broadleaf and grass weed control with safety to plantation crops such as coffee, cocoa, oil palm, rubber, banana, citrus and certain conifers.

Compound I can be applied as a preemergence or postemergence treatment using techniques of banding, directed sprays or broadcast applications. In general, the compound of this invention is used at 0.5 to 500 g/ha with a preferred rate range of 1 to 250 g/ha rate. One skilled in the art can select the proper rates for a given situation.

The compound of this invention may be used in combination with other pesticides. It is particularly useful in combination with broadleaf herbicides used in plantation crops including: triazine, triazole, uracil, urea, amide, carbamate, bipyridylium, phenoxys, sulfonylurea and imidazolinone types.

The preferred mixture for use in plantation crops includes glyphosate and its agriculturally suitable salts.

The herbicidal properties of the subject compound were discovered in field tests conducted as described below.

TEST A

This test was conducted in the field with the postemergence spraying of circles around oil palm. The weed species, *Calopogonium caerulium* (A), *Mikania micrantha* (B) and *Paspalum conjugatum* (C) ranged in height from 10–20 cm up to mature plants and were sprayed with Compound I or its mixtures with Compounds II and III, dissolved in a nonphytotoxic solvent containing a surfactant. The degree of weed control was visually rated 0 to 125 days after treatment. The control ratings are averages of the readings and are expressed on a scale of 0 to 100 where 0=no effect, 20=minimal control and 100=complete control. The results are summarized in Table A.

Compound II—1,1'-dimethyl-4,4'-bipyridinium ion
Compound III—mono(isopropylammonium)N-(phosphonomethyl)glycine.

TABLE A

| | Weed Control in Oil Palm | | |
|---|---|---|---|
| Treatment | Average Control Rating | | |
| Compound (g/ha) | A | B | C |
| I(10) + II (990) | 99 | 48 | 41 |
| I(10) | 75 | 1.4 | 0 |
| I(II) + III (615) | 91 | 40 | 61 |
| I(20) + II (990) | 100 | 60 | 36 |
| I(20) | 90 | 1.2 | 0 |
| I(20) + III (615) | 97 | 41 | 95 |

TEST B

This test was conducted in the field with the postemergence spraying of strips in rubber. The weed species *Borreria latifolia, Clidemia hirta, Dicranopteris linearis, Eupatorium odoratum, Euphorbia heterophylla, Imperata cylindrica, Lantana camara, Melastoma malabathricum, Nephrolepis biserrata* and *Pennisetum pedicellatum* ranged in height from 10–20 cm up to mature plants and were sprayed with Compound I or its mixtures with Compounds II and III, dissolved in a nonphytotoxic solvents containing a surfactant. The degree of weed control was visually rated 0 to 125 days after treatment. The control ratings are averages of the readings and are expressed on a scale of 0 to 100 where 0=no effect, 20=minimal control and 100= complete control. The results are summarized in Tables B to K.

Compound II—1,1'-dimethyl-4,4'-bipyridinium ion

Compound III—mono(isopropylammonium)N-(phosphonomethyl)glycine.

TABLE B

| Weed Control in Rubber | |
|---|---|
| Treatment Compound (g/ha) | Average Control Rating *Borreria latifolia* |
| I (15) | 80 |
| I (15) + II (550) | 97 |
| I (15) + III (1250) | 96 |
| I (15) + III (625) | 94 |
| I (15) + III (835) | 95 |
| I (20) | 84 |
| I (20) + II (550) | 98 |
| I (20) + III (1250) | 97 |
| I (30) | 83 |
| I (30) + II (550) | 98 |
| I (30) + III (1250) | 99 |
| I (40) | 83 |
| I (40) + II (550) | 99 |
| I (40) + III (1250) | 99 |
| I (90) | 83 |

TABLE C

| Weed Control in Rubber | |
|---|---|
| Treatment Compound (g/ha) | Average Control Rating *Clidemia hirta* |
| I (10) | 71 |
| I (10) + II (990) | 69 |
| I (20) | 90 |
| I (20) + II (990) | 78 |
| I (40) | 96 |
| I (40) + II (990) | 87 |
| I (5) | 40 |
| I (5) + II (990) | 85 |

TABLE D

| Weed Control in Rubber | |
|---|---|
| Treatment Compound (g/ha) | Average Control Rating *Dicranopteris linearis* |
| I (10) + II (445) | 96 |
| I (10) | 65 |
| I (20) + II (445) | 97 |
| I (20) | 58 |

TABLE E

| Weed Control in Rubber | |
|---|---|
| Treatment Compound (g/ha) | Average Control Rating *Eupatorium odoratum* |
| I (10) | 29 |
| I (10) + II (990) | 67 |
| I (15) | 34 |
| I (15) + III (615) | 56 |
| I (20) | 35 |
| I (20) + II (990) | 69 |
| I (20) + III (615) | 61 |
| I (25) | 50 |
| I (30) | 48 |
| I (30) + III (615) | 70 |
| I (35) | 47 |
| I (40) | 48 |

TABLE F

| Weed Control in Rubber | |
|---|---|
| Treatment Compound (g/ha) | Average Control Rating *Euphorbia heterophylla* |
| I (15) | 61 |
| I (15) + II (550) | 88 |
| I (15) + III (1250) | 90 |
| I (15) + III (625) | 77 |
| I (15) + III (835) | 85 |
| I (20) | 48 |
| I (20) + II (550) | 91 |
| I (20) + III (1250) | 96 |
| I (30) | 46 |
| I (30) + II (550) | 96 |
| I (30) + III (1250) | 97 |
| I (40) | 46 |
| I (40) + II (550) | 99 |
| I (40) + III (1250) | 95 |
| I (90) | 80 |

TABLE G

| Weed Control in Rubber | |
|---|---|
| Treatment Compound (g/ha) | Average Control Rating *Imperata cylindrica* |
| I (15) | 0 |
| I (15) + II (550) | 88 |
| I (15) + III (1250) | 90 |
| I (20) | 0 |
| I (20) + II (550) | 91 |
| I (20) + III (1250) | 90 |
| I (30) | 0 |
| I (30) + II (550) | 85 |
| I (30) + III (1250) | 83 |
| I (40) | 0 |
| I (40) + II (550) | 94 |
| I (40) + III (1250) | 48 |

TABLE H

| Weed Control in Rubber | |
|---|---|
| Treatment Compound (g/ha) | Average Control Rating *Lantana camara* |
| I (10) | 93 |
| I (20) | 98 |

TABLE I

| Weed Control in Rubber | |
|---|---|
| Treatment Compound (g/ha) | Average Control Rating *Melastoma malabathricum* |
| I (10) | 94 |
| I (10) + II (990) | 73 |
| I (20) | 97 |
| I (20) + II (990) | 81 |
| I (40) | 98 |

TABLE J

| Weed Control in Rubber | |
|---|---|
| Treatment Compound (g/ha) | Average Control Rating *Nephrolepis biserrata* |
| I (10) + II (445) | 92 |
| I (10) | 48 |
| I (20) + II (445) | 92 |
| I (20) | 62 |

TABLE K

Weed Control in Rubber

| Treatment Compound (g/ha) | Average Control Rating Pennisetum pedicellatum |
|---|---|
| I (15) | 68 |
| I (15) + II (550) | 97 |
| I (15) + III (1250) | 100 |
| I (20) | 66 |
| I (20) + II (550) | 96 |
| I (20) + III (1250) | 100 |
| I (30) | 62 |
| I (30) + II (550) | 82 |
| I (30) + III (1250) | 100 |
| I (40) | 56 |
| I (40) + II (550) | 99 |
| I (40) + III (1250) | 100 |

What is claimed is:

1. A method for controlling undesired weeds in plantation crops which comprises applying to the locus of the weeds a herbicidally effective amount of methyl 2-[[[[(4-methoxy-6-methyl-1,3,5-triazin-2-yl)amino]carbonyl]amino]sulfonyl]benzoate, the plantation crops selected from the group consisting of coffee, cocoa, oil palm, rubber, banana and citrus.

2. A method according to claim 1 wherein the plantation crop is rubber or oil palm.

3. A method according to claim 2 wherein the plantation crop is rubber.

4. A method according to claim 2 wherein the plantation crop is oil palm.

* * * * *